United States Patent [19]
Materne et al.

[11] Patent Number: 6,096,832
[45] Date of Patent: Aug. 1, 2000

[54] ASYMMETRICAL SILOXY COMPOUNDS

[75] Inventors: Thierry Florent Edme Materne, Akron, Ohio; Giorgio Agostini, Colmar-Berg; Friedrich Visel, Bofferdange, both of Luxembourg; Martin Paul Cohen, Fairlawn, Ohio

[73] Assignee: The Goodyear Tire & Rubber Company, Akron, Ohio

[21] Appl. No.: 09/252,517

[22] Filed: Feb. 18, 1999

Related U.S. Application Data
[60] Provisional application No. 60/076,382, Feb. 26, 1998.

[51] Int. Cl.$^7$ .............................. C08K 5/54; C08C 19/22; C07F 7/10
[52] U.S. Cl. ..................... 525/332.7; 524/262; 524/86; 524/188; 525/343; 525/347; 525/351; 525/374; 525/375; 523/213; 556/442
[58] Field of Search .................... 524/262, 86, 188; 525/332.7, 343, 347, 351, 374, 375; 523/213; 556/422

[56] References Cited

U.S. PATENT DOCUMENTS 5,037,872  8/1991  Schwarze et al. ................ 525/332.7
5,916,973  6/1999  Zimmer et al. .................... 525/236

*Primary Examiner*—James J. Seidleck
*Assistant Examiner*—Olga Asinovsky
*Attorney, Agent, or Firm*—Bruce J Hendricks

[57] ABSTRACT

The present invention relates to asymmetrical siloxy compounds of the formula

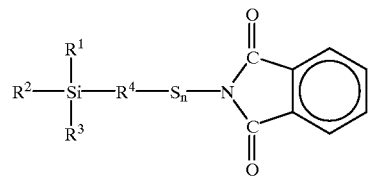

I wherein $R^1$, $R^2$ and $R^3$ are independently selected from the group consisting of alkoxy radicals having from 1 to 8 carbon atoms; $R^4$ is selected from the group consisting of alkylene groups having from 1 to 15 carbon atoms and arylene and alkyl substituted arylene groups having from 6 to 10 carbon atoms; and n is an integer of from 1 to 8.

10 Claims, No Drawings

ASYMMETRICAL SILOXY COMPOUNDS

This application claims the benefit of U.S. Provisional Application 60/076,382 filed Feb. 26, 1998.

FIELD OF THE INVENTION

The present invention relates to a compound which is useful in silica-filled rubber compositions and the processing of a sulfur curable rubber composition containing silica.

BACKGROUND OF THE INVENTION

Sulfur containing organosilicon compounds are useful as reactive coupling agents between rubber and silica fillers providing for improved physical properties. They are also useful as adhesion primers for glass, metals and other substrates.

U.S. Pat. Nos. 3,842,111, 3,873,489 and 3,978,103 disclose the preparation of various sulfur containing organosilicon compounds. These organosilicon compounds are prepared by reacting
(a) 2 moles of a compound of the formula Z-Alk-hal where hal is a chlorine, bromine or iodine; Z is

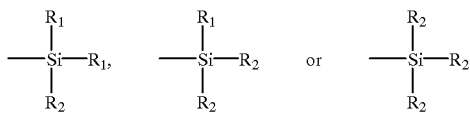

where $R_1$ is an alkyl of 1 to 4 carbon atoms or phenyl and $R_2$ is alkoxy of 1 to 8 carbon atoms; or cycloalkoxy of 5 to 8 carbon atoms; or alkylmercapto with 1 to 8 carbon atoms; Alk is a divalent aliphatic hydrocarbon or unsaturated hydrocarbon or a cyclic hydrocarbon containing 1 to 18 carbon atoms; with
(b) 1 mole of a compound of the formula Me$_2$S$_n$ where Me is ammonium or a metal atom and n is a whole number from 2 to 6.

U.S. Pat. No. 4,820,751 and Japanese Patent Application 124400-1984 disclose the use of an asymmetrical siloxy compound in a silica-filled rubber. Representative asymmetrical siloxy compounds contain a benzothizole moiety or thiocarbamyl moiety.

SUMMARY OF THE INVENTION

The present invention relates to asymmetrical siloxy compounds of the formula:

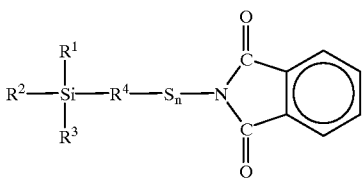

DETAILED DESCRIPTION OF THE INVENTION

There is also disclosed a method for processing a silica-filled rubber composition which comprises mixing (i) 100 parts by weight of at least one sulfur vulcanizable elastomer selected from conjugated diene homopolymers and copolymers and from copolymers of at least one conjugated diene and aromatic vinyl compound;
(ii) 10 to 250 phr of particulate precipitated silica;
(iii) 0.05 to 15 phr of a compound of the formula

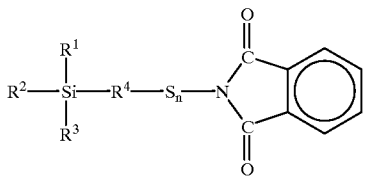

wherein $R^1$, $R^2$ and $R^3$ are independently selected from the group consisting of alkoxy radicals having from 1 to 8 carbon atoms; $R^4$ is selected from the group consisting of alkylene groups having from 1 to 15 carbon atoms and arylene and alkyl substituted arylene groups having from 6 to 10 carbon atoms; and n is an integer of from 1 to 8.

There is also disclosed a silica-filled rubber composition comprising an elastomer containing olefinic unsaturation, silica and a compound of the formula

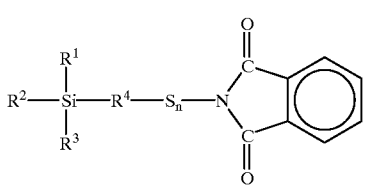

wherein $R^1$, $R^2$ and $R^3$ are independently selected from the group consisting of alkoxy radicals having from 1 to 8 carbon atoms; $R^4$ is selected from the group consisting of alkylene groups having from 1 to 15 carbon atoms and arylene and alkyl substituted arylene groups having from 6 to 10 carbon atoms; and n is an integer of from 1 to 8.

The present invention may be used to process rubbers or elastomers containing olefinic unsaturation. The phrase "rubber or elastomer containing olefinic unsaturation" is intended to include both natural rubber and its various raw and reclaim forms as well as various synthetic rubbers. In the description of this invention, the terms "rubber" and "elastomer" may be used interchangeably, unless otherwise prescribed. The terms "rubber composition", "compounded rubber" and "rubber compound" are used interchangeably to refer to rubber which has been blended or mixed with various ingredients and materials and such terms are well known to those having skill in the rubber mixing or rubber compounding art. Representative synthetic polymers are the homopolymerization products of butadiene and its homologues and derivatives, for example, methylbutadiene, dimethylbutadiene and pentadiene as well as copolymers such as those formed from butadiene or its homologues or derivatives with other unsaturated monomers. Among the latter are acetylenes, for example, vinyl acetylene; olefins, for example, isobutylene, which copolymerizes with isoprene to form butyl rubber; vinyl compounds, for example, acrylic acid, acrylonitrile (which polymerize with butadiene to form NBR), methacrylic acid and styrene, the latter compound polymerizing with butadiene to form SBR, as well as vinyl esters and various unsaturated aldehydes, ketones and ethers, e.g., acrolein, methyl isopropenyl ketone and vinyl-ethyl ether. Specific examples of synthetic rubbers include neoprene (polychloroprene), polybutadiene (including cis-1,4-polybutadiene), polyisoprene (including cis-1,4-polyisoprene), butyl rubber, styrene/isoprene/butadiene rubber, copolymers of 1,3-butadiene or isoprene with monomers such as styrene, acrylonitrile and methyl methacrylate, as well as ethylene/propylene terpolymers, also known as ethylene/propylene/diene monomer (EPDM), and in particular, ethylene/propylene/dicyclopentadiene terpolymers. The preferred rubber or elastomers are polybutadiene and SBR.

In one aspect the rubber is preferably of at least two of diene based rubbers. For example, a combination of two or more rubbers is preferred such as cis 1,4-polyisoprene rubber (natural or synthetic, although natural is preferred), 3,4-polyisoprene rubber, styrene/isoprene/butadiene rubber, emulsion and solution polymerization derived styrene/butadiene rubbers, cis 1,4-polybutadiene rubbers and emulsion polymerization prepared butadiene/acrylonitrile copolymers.

In one aspect of this invention, an emulsion polymerization derived styrene/butadiene (E-SBR) might be used having a relatively conventional styrene content of about 20 to about 28 percent bound styrene or, for some applications, an E-SBR having a medium to relatively high bound styrene content, namely, a bound styrene content of about 30 to about 45 percent.

The relatively high styrene content of about 30 to about 45 for the E-SBR can be considered beneficial for a purpose of enhancing traction, or skid resistance, of the tire tread. The presence of the E-SBR itself is considered beneficial for a purpose of enhancing processability of the uncured elastomer composition mixture, especially in comparison to a utilization of a solution polymerization prepared SBR (S-SBR).

By emulsion polymerization prepared E-SBR, it is meant that styrene and 1,3-butadiene are copolymerized as an aqueous emulsion. Such are well known to those skilled in such art. The bound styrene content can vary, for example, from about 5 to about 50 percent. In one aspect, the E-SBR may also contain acrylonitrile to form a terpolymer rubber, as E-SBAR, in amounts, for example, of about 2 to about 30 weight percent bound acrylonitrile in the terpolymer.

Emulsion polymerization prepared styrene/butadiene/acrylonitrile copolymer rubbers containing about 2 to about 40 weight percent bound acrylonitrile in the copolymer are also contemplated as diene based rubbers for use in this invention.

The solution polymerization prepared SBR (S-SBR) typically has a bound styrene content in a range of about 5 to about 50, preferably about 9 to about 36, percent. The S-SBR can be conveniently prepared, for example, by organo lithium catalyzation in the presence of an organic hydrocarbon solvent.

A purpose of using S-SBR is for improved tire rolling resistance as a result of lower hysteresis when it is used in a tire tread composition.

The 3,4-polyisoprene rubber (3,4-PI) is considered beneficial for a purpose of enhancing the tire's traction when it is used in a tire tread composition. The 3,4-PI and use thereof is more fully described in U.S. Pat. No. 5,087,668 which is incorporated herein by reference. The Tg refers to the glass transition temperature which can conveniently be determined by a differential scanning calorimeter at a heating rate of 10° C. per minute.

The cis 1,4-polybutadiene rubber (BR) is considered to be beneficial for a purpose of enhancing the tire tread's wear, or treadwear. Such BR can be prepared, for example, by organic solution polymerization of 1,3-butadiene. The BR may be conveniently characterized, for example, by having at least a 90 percent cis 1,4-content.

The cis 1,4-polyisoprene and cis 1,4-polyisoprene natural rubber are well known to those having skill in the rubber art.

The term "phr" as used herein, and according to conventional practice, refers to "parts by weight of a respective material per 100 parts by weight of rubber, or elastomer."

The asymmetrical siloxy compounds of the present invention are of the formula

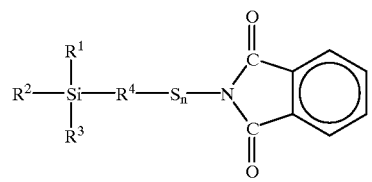

wherein $R^1$, $R^2$ and $R^3$ are independently selected from the group consisting of alkoxy radicals having from 1 to 8 carbon atoms; $R^4$ is selected from the group consisting of alkylene groups having from 1 to 15 carbon atoms and arylene and alkyl substituted arylene groups having from 6 to 10 carbon atoms; and n is an integer of from 1 to 8. Preferably, each $R^1$, $R^2$ and $R^3$ are alkoxy radicals having from 1 to 3 carbon atoms, $R^4$ is an alkylene group having from 1 to 3 carbon atoms and n is an integer of from 1 to 4. The asymmetrical siloxy compounds may comprise a high purity product or mixture of products conforming to the above formula.

The asymmetrical siloxy compounds may be classified as trialkoxysilylalkyl-phthalimide-sulfides and trialkoxysilylaryl-phthalimide-sulfides. Specific examples include the triethoxysilylpropyl-phthalimide-monosulfide, triethoxysilylpropyl-phthalimide-disulfide, triethoxysilylpropyl-phthalimide-tetrasulfide, triethoxysilylpropyl-phthalimide-hexasulfide and triethoxysilylpropyl-phthalimide-octasulfide.

The compounds of Formula I where "n" is 1 may be prepared according to the reaction scheme listed below.

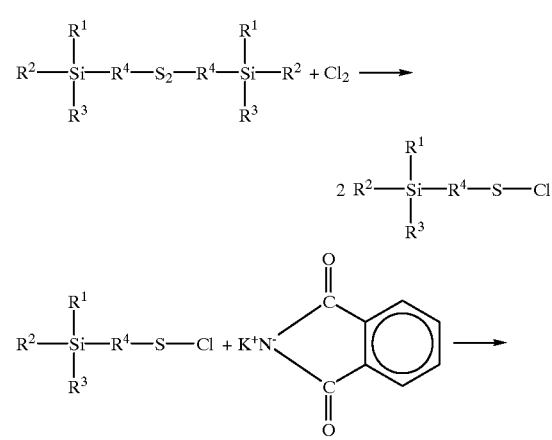

-continued

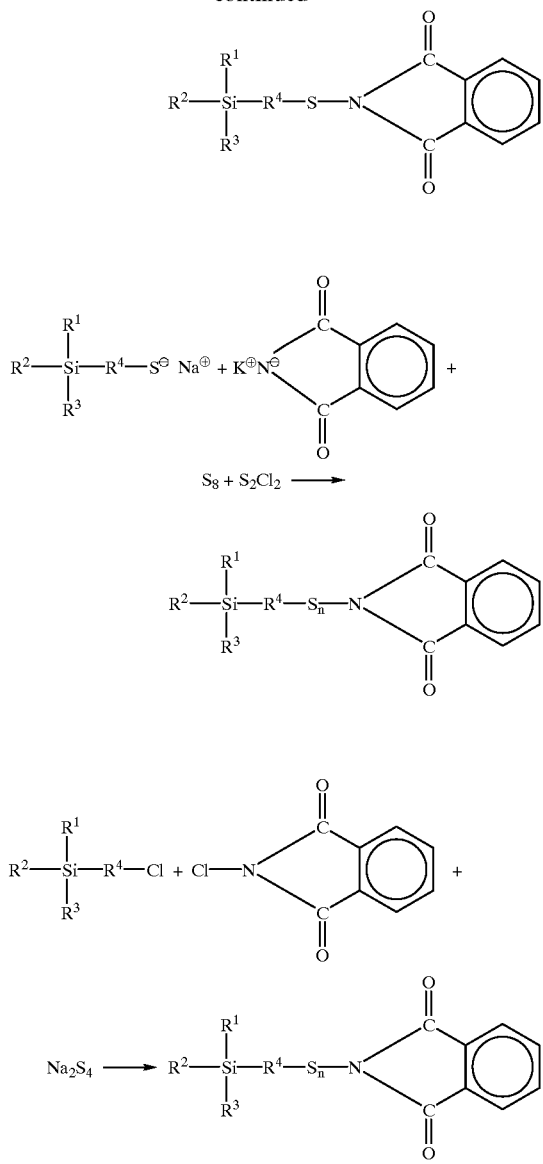

The above reactions are generally conducted in the presence of a suitable solvent. The primary criterion is to use a solvent which does not react with the starting materials or end product. Representative organic solvents include chloroform, dichloromethane, carbon tetrachloride, hexane, heptane, cyclohexane, xylene, benzene and toluene. Preferably, water is avoided to prevent reaction with the siloxy groups, halogen containing intermediates as well as any halogen reagents.

The asymmetrical siloxy compounds used in the present invention may be added to the rubber by any conventional technique such as on a mill or in a Banbury. The amount of the asymmetrical siloxy compound may vary widely depending on the type of rubber and other compounds present in the vulcanizable composition. Generally, the amount of the siloxy compound is used in a range of from about 0.05 to about 15.0 phr with a range of 0.1 to about 8.0 phr being preferred. The siloxy compound is preferably added in the nonproductive stage with the silica.

For ease in handling, the asymmetrical siloxy compound may be used per se or may be deposited on suitable carriers.

Examples of carriers which may be used in the present invention include silica, carbon black, alumina, alumina silicates, clay, kieselguhr, cellulose, silica gel and calcium silicate.

The rubber composition should contain a sufficient amount of silica, and carbon black, if used, to contribute a reasonably high modulus and high resistance to tear. The silica filler may be added in amounts ranging from 10 to 250 phr. Preferably, the silica is present in an amount ranging from 15 to 90 phr. If carbon black is also present, the amount of carbon black, if used, may vary. Generally speaking, the amount of carbon black will vary from 0 to 80 phr. Preferably, the amount of carbon black will range from 0 to 40 phr. It is to be appreciated that the silica coupler may be used in conjunction with a carbon black, namely pre-mixed with a carbon black prior to addition to the rubber composition, and such carbon black is to be included in the aforesaid amount of carbon black for the rubber composition formulation.

The commonly employed siliceous pigments used in rubber compounding applications can be used as the silica in this invention, including pyrogenic and precipitated siliceous pigments (silica) and aluminosilicates, although precipitate silicas are preferred. The siliceous pigments preferably employed in this invention are precipitated silicas such as, for example, those obtained by the acidification of a soluble silicate, e.g., sodium silicate.

Such silicas might be characterized, for example, by having a BET surface area, as measured using nitrogen gas, preferably in the range of about 40 to about 600, and more usually in a range of about 50 to about 300 square meters per gram. The BET method of measuring surface area is described in the *Journal of the American Chemical Society*, Volume 60, page 304 (1930).

The silica may also be typically characterized by having a dibutylphthalate (DBP) absorption value in a range of about 100 to about 400, and more usually about 150 to about 300.

Further, the silica, as well as the aforesaid alumina and aluminosilicate may be expected to have a CTAB surface area in a range of about 100 to about 220. The CTAB surface area is the external surface area as evaluated by cetyl trimethylammonium bromide with a pH of 9. The method is described in ASTM D 3849 for set up and evaluation. The CTAB surface area is a well known means for characterization of silica.

Mercury surface area/porosity is the specific surface area determined by Mercury porosimetry. For such technique, mercury is penetrated into the pores of the sample after a thermal treatment to remove volatiles. Set-up conditions may be suitably described as using a 100 mg sample; removing volatiles during 2 hours at 105° C. and ambient atmospheric pressure; ambient to 2000 bars pressure measuring range. Such evaluation may be performed according to the method described in Winslow, Shapiro in ASTM bulletin, p.39 (1959) or according to DIN 66133. For such an evaluation, a CARLO-ERBA Porosimeter 2000 might be used.

The average mercury porosity specific surface area for the silica should be in a range of about 100 to 300 m$^2$/g.

A suitable pore-size distribution for the silica, alumina and aluminosilicate according to such mercury porosity evaluation is considered herein to be five percent or less of its pores have a diameter of less than about 10 nm; 60 to 90 percent of its pores have a diameter of about 10 to about 100 nm; 10 to 30 percent of its pores have a diameter of about 100 to about 1000 nm; and 5 to 20 percent of its pores have a diameter of greater than about 1000 nm.

The silica might be expected to have an average ultimate particle size, for example, in the range of 0.01 to 0.05 micron as determined by the electron microscope, although the silica particles may be even smaller, or possibly larger, in size.

Various commercially available silicas may be considered for use in this invention such as, only for example herein, and without limitation, silicas commercially available from PPG Industries under the Hi-Sil trademark with designations 210, 243, etc; silicas available from Rhone-Poulenc, with, for example, designations of Z1165MP and Z165GR; and silicas available from Degussa AG with, for example, designations VN2, VN3, BV3380GR, etc; and silicas available from Huber, for example Huber Sil 8745.

The asymmetrical siloxy compounds of Formula I function as silica coupling agents. They may be used alone and/or in combination with additional sulfur containing organosilicon compounds. Examples of suitable sulfur containing organosilicon compounds are of the formula:

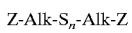

Z-Alk-S$_n$-Alk-Z    II in which Z is selected from the group consisting of

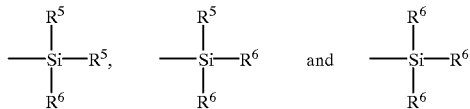

where R$^5$ is an alkyl group of 1 to 4 carbon atoms, cyclohexyl or phenyl;

R$^6$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8.

Specific examples of sulfur containing organosilicon compounds of Formula II which may be used in accordance with the present invention include: 3,3'-bis (trimethoxysilylpropyl) disulfide, 3,3'-bis (triethoxysilylpropyl) disulfide, 3,3'-bis (triethoxysilylpropyl) tetrasulfide, 3,3'-bis (triethoxysilylpropyl) octasulfide, 3,3'-bis (trimethoxysilylpropyl) tetrasulfide, 2,2'-bis (triethoxysilylethyl) tetrasulfide, 3,3'-bis (trimethoxysilylpropyl) trisulfide, 3,3'-bis (triethoxysilylpropyl) trisulfide, 3,3'-bis (tributoxysilylpropyl) disulfide, 3,3'-bis (trimethoxysilylpropyl) hexasulfide, 3,3'-bis (trimethoxysilylpropyl) octasulfide, 3,3'-bis (trioctoxysilylpropyl) tetrasulfide, 3,3'-bis (trihexoxysilylpropyl) disulfide, 3,3'-bis(tri-2"-ethylhexoxysilylpropyl) trisulfide, 3,3'-bis (triisooctoxysilylpropyl) tetrasulfide, 3,3'-bis(tri-t-butoxysilylpropyl) disulfide, 2,2'-bis(methoxy diethoxy silyl ethyl) tetrasulfide, 2,2'-bis (tripropoxysilylethyl) pentasulfide, 3,3'-bis(tricyclonexoxysilylpropyl) tetrasulfide, 3,3'-bis(tricyclopentoxysilylpropyl) trisulfide, 2,2'-bis(tri-2"-methylcyclohexoxysilylethyl) tetrasulfide, bis (trimethoxysilylmethyl) tetrasulfide, 3-methoxy ethoxy propoxysilyl 3'-diethoxybutoxy-silylpropyltetrasulfide, 2,2'-bis (dimethyl methoxysilylethyl) disulfide, 2,2'-bis(dimethyl sec.butoxysilylethyl) trisulfide, 3,3'-bis(methyl butylethoxysilylpropyl) tetrasulfide, 3,3'-bis(di t-butylmethoxysilylpropyl) tetrasulfide, 2,2'-bis(phenyl methyl methoxysilylethyl) trisulfide, 3,3'-bis(diphenyl isopropoxysilylpropyl) tetrasulfide, 3,3'-bis(diphenyl cyclohexoxysilylpropyl) disulfide, 3,3'-bis(dimethyl ethylmercaptosilylpropyl) tetrasulfide, 2,2'-bis(methyl dimethoxysilylethyl) trisulfide, 2,2'-bis(methyl ethoxypropoxysilylethyl) tetrasulfide, 3,3'-bis(diethyl methoxysilylpropyl) tetrasulfide, 3,3'-bis(ethyl di-sec. butoxysilylpropyl) disulfide, 3,3'-bis(propyl diethoxysilylpropyl) disulfide, 3,3'-bis(butyl dimethoxysilylpropyl) trisulfide, 3,3'-bis(phenyl dimethoxysilylpropyl) tetrasulfide, 3-phenyl ethoxybutoxysilyl 3'-trimethoxysilylpropyl tetrasulfide, 4,4'-bis (trimethoxysilylbutyl) tetrasulfide, 6,6'-bis (triethoxysilylhexyl) tetrasulfide, 12,12'-bis (triisopropoxysilyl dodecyl) disulfide, 18,18'-bis (trimethoxysilyloctadecyl) tetrasulfide, 18,18'-bis (tripropoxysilyloctadecenyl) tetrasulfide, 4,4'-bis (trimethoxysilyl-buten-2-yl) tetrasulfide, 4,4'-bis (trimethoxysilylcyclohexylene) tetrasulfide, 5,5'-bis (dimethoxymethylsilylpentyl) trisulfide, 3,3,-bis (trimethoxysilyl-2-methylpropyl) tetrasulfide, 3,3,-bis (dimethoxyphenylsilyl-2-methylpropyl) disulfide.

The preferred sulfur containing organosilicon compounds of Formula II are the 3,3'-bis(trimethoxy or triethoxy silylpropyl) sulfides. The most preferred compounds are 3,3'-bis(triethoxysilylpropyl) tetrasulfide and 3,3'-bis (triethoxysilylpropyl) disulfide. Preferably Z is

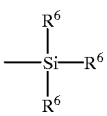

where R$^6$ is an alkoxy of 2 to 4 carbon atoms, with 2 carbon atoms being particularly preferred; Alk is a divalent hydrocarbon of 2 to 4 carbon atoms with 3 carbon atoms being particularly preferred; and n is an integer of from 2 to 4.

The amount of the above sulfur containing organosilicon compound of Formula II in a rubber composition will vary depending on the level of silica that is used. Generally speaking, the amount of the compound of Formula II will range from 0.00 to 1.0 parts by weight per part by weight of the silica. Preferably, the amount will range from 0.00 to 0.4 parts by weight per part by weight of the silica.

It is readily understood by those having skill in the art that the rubber composition would be compounded by methods generally known in the rubber compounding art, such as mixing the various sulfur-vulcanizable constituent rubbers with various commonly used additive materials such as, for example, sulfur donors, curing aids, such as activators and retarders and processing additives, such as oils, resins including tackifying resins and plasticizers, fillers, pigments, fatty acid, zinc oxide, waxes, antioxidants and antiozonants and peptizing agents. As known to those skilled in the art, depending on the intended use of the sulfur vulcanizable and sulfur vulcanized material (rubbers), the additives mentioned above are selected and commonly used in conventional amounts. Typical amounts of reinforcing type carbon blacks(s), for this invention, if used, are herein set forth. Representative examples of sulfur donors include elemental sulfur (free sulfur), an amine disulfide, polymeric polysulfide and sulfur olefin adducts. Preferably, the sulfur vulcanizing agent is elemental sulfur. The sulfur vulcanizing agent may be used in an amount ranging from 0.5 to 8 phr, with a range of from 1 to 6 phr being preferred. Typical amounts of tackifier resins, if used, comprise about 0.5 to about 10 phr, usually about 1 to about 5 phr. Typical amounts of processing aids comprise about 1 to about 50 phr. Such processing aids can include, for example, aromatic, napthenic, and/or paraffinic processing oils. Typical amounts of antioxidants comprise about 1 to about 5 phr. Representative antioxidants may be, for example, diphenyl-p-phenylenediamine and others, such as, for example, those disclosed in the *Vanderbilt Rubber Handbook* (1978), pages 344–346. Typical amounts of antiozonants comprise about 1 to 5 phr. Typical amounts of fatty acids, if used, which can include stearic acid, comprise about 0.5 to about 5 phr. Typical amounts of zinc oxide comprise about 2 to about 5 phr. Typical amounts of waxes comprise about 1 to about 5 phr. Often microcrystalline waxes are used. Typical amounts of peptizers comprise about 0.1 to about 1 phr. Typical peptizers may be, for example, pentachlorothiophenol and dibenzamidodiphenyl disulfide.

In one aspect of the present invention, the sulfur vulcanizable rubber composition is then sulfur-cured or vulcanized.

Accelerators are used to control the time and/or temperature required for vulcanization and to improve the properties of the vulcanizate. In one embodiment, a single accelerator system may be used, i.e., primary accelerator. The primary accelerator(s) may be used in total amounts ranging from about 0.5 to about 4, preferably about 0.8 to about 1.5, phr. In another embodiment, combinations of a primary and a secondary accelerator might be used with the secondary accelerator being used in amounts, such as from about 0.05 to about 3 phr, in order to activate and to improve the properties of the vulcanizate. Combinations of these accelerators might be expected to produce a synergistic effect on the final properties and are somewhat better than those produced by use of either accelerator alone. In addition, delayed action accelerators may be used which are not affected by normal processing temperatures but produce a satisfactory cure at ordinary vulcanization temperatures. Vulcanization retarders might also be used. Suitable types of accelerators that may be used in the present invention are amines, disulfides, guanidines, thioureas, thiazoles, thiurams, sulfenamides, dithiocarbamates and xanthates. Preferably, the primary accelerator is a sulfenamide. If a second accelerator is used, the secondary accelerator is preferably a guanidine, dithiocarbamate or thiuram compound.

The mixing of the rubber composition can be accomplished by methods known to those having skill in the rubber mixing art. For example, the ingredients are typically mixed in at least two stages, namely at least one non-productive stage followed by a productive mix stage. The final curatives including sulfur vulcanizing agents are typically mixed in the final stage which is conventionally called the "productive" mix stage in which the mixing typically occurs at a temperature, or ultimate temperature, lower than the mix temperature(s) than the preceding non-productive mix stage (s). The rubber, silica, compound of Formula I and carbon black, if used, are mixed in one or more non-productive mix stages. The terms "non-productive" and "productive" mix stages are well known to those having skill in the rubber mixing art. The sulfur vulcanizable rubber composition containing the compound of Formula I, vulcanizable rubber and generally at least part of the silica should, as well as the sulfur-containing organosilicon compound of Formula II, if used, be subjected to a thermomechanical mixing step. The thermomechanical mixing step generally comprises a mechanical working in a mixer or extruder for a period of time suitable in order to produce a rubber temperature between 140° C. and 190° C. The appropriate duration of the thermomechanical working varies as a function of the operating conditions and the volume and nature of the components. For example, the thermomechanical working may be from 1 to 20 minutes.

In such manner, then the asymmetrical siloxy compound could be utilized for reaction with the silica and sulfur vulcanizable elastomer and the independent addition of the sulfur donor, particularly a free sulfur source, could be primarily relied upon for the vulcanization of the elastomer.

In accordance with another embodiment, the asymmetrical siloxy compound is optionally added to the thermomechanical preparatory mixing in a form of a particulate comprised of (a) about 25 to about 75, preferably about 40 to about 60, weight percent of said asymmetrical siloxy compound and, correspondingly, (b) about 75 to about 25, preferably about 60 to about 40, weight percent particulate carbon black. One advantage of this embodiment is providing the asymmetrical siloxy compound in a form of a particulate so as to add the asymmetrical siloxy compound in a form of a relatively dry, or substantially dry, powder in which the carbon black acts as a carrier for the asymmetrical siloxy compound since it is considered herein that the asymmetrical siloxy compound may be liquid, or substantially liquid. A contemplated benefit for the particulate is to aid in the dispersing of the asymmetrical siloxy compound in the preparatory mixing step(s) of the process of this invention and to aid in the introduction of the asymmetrical siloxy compound into the preparatory mixing of the rubber composition mixture.

Accordingly, the invention also thereby contemplates a vulcanized rubber composition prepared by such process.

Accordingly, the invention also thereby contemplates a vulcanized tire prepared by such process.

Vulcanization of the rubber composition of the present invention is generally carried out at conventional temperatures ranging from about 100° C. to 200° C. Preferably, the vulcanization is conducted at temperatures ranging from about 110° C. to 180° C. Any of the usual vulcanization processes may be used such as heating in a press or mold, heating with superheated steam or hot air or in a salt bath.

Upon vulcanization of the sulfur vulcanized composition, the rubber composition of this invention can be used for various purposes. For example, the sulfur vulcanized rubber composition may be in the form of a tire, belt or hose. In case of a tire, it can be used for various tire components. Such tires can be built, shaped, molded and cured by various methods which are known and will be readily apparent to those having skill in such art. Preferably, the rubber composition is used in the tread of a tire. As can be appreciated, the tire may be a passenger tire, aircraft tire, truck tire and the like. Preferably, the tire is a passenger tire. The tire may also be a radial or bias, with a radial tire being preferred.

While certain representative embodiments and details have been shown for the purpose of illustrating the invention, it will be apparent to those skilled in this art that various changes and modifications may be made therein without departing from the spirit or scope of the invention.

What is claimed is:

1. A sulfur vulcanizable rubber composition comprising an elastomer containing olefinic unsaturation, silica and a compound of the formula

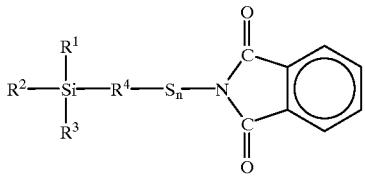

wherein $R^1$, $R^2$ and $R^3$ are independently selected from the group consisting of alkoxy radicals having from 1 to 8 carbon atoms; $R^4$ is selected from the group consisting of alkylene groups having from 1 to 15 carbon atoms and arylene and alkyl substituted arylene groups having from 6 to 10 carbon atoms; and n is an integer of from 1 to 8.

2. The composition of claim 1 wherein each $R^1$, $R^2$ and $R^3$ are alkoxy radicals having 1 to 3 carbon atoms, $R^4$ is an alkylene group having 1 to 3 carbon atoms and n is an integer of from 1 to 4.

3. The composition of claim 1 wherein n is 1.

4. The composition of claim 1 wherein n is 2 to 4.

5. The composition of claim 1 wherein said asymmetrical siloxy compound is present in an amount ranging from 0.05 to 15.0 phr.

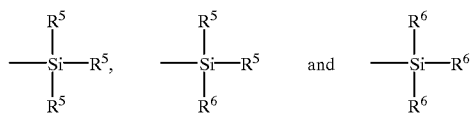

where $R^5$ is an alkyl group of 1 to 4 carbon atoms, cyclohexyl or phenyl; $R^6$ is alkoxy of 1 to 8 carbon atoms, or cycloalkoxy of 5 to 8 carbon atoms; Alk is a divalent hydrocarbon of 1 to 18 carbon atoms and n is an integer of 2 to 8.

6. The composition of claim 1 wherein said silica is present in an amount ranging from 10 to 250 phr.

7. The composition of claim 1 wherein said elastomer containing olefinic unsaturation is selected from the group consisting of natural rubber, neoprene, polyisoprene, butyl rubber, polybutadiene, styrene-butadiene copolymer, styrene/isoprene/butadiene rubber, methyl methacrylate-butadiene copolymer, isoprene-styrene copolymer, methyl methacrylate-isoprene copolymer, acrylonitrile-isoprene copolymer, acrylonitrile-butadiene copolymer, EPDM and mixtures thereof.

8. The composition of claim 1 wherein said composition was thermomechanically mixed at a rubber temperature in a range of from 140° C. to 190° C. for a total mixing time of from 1 to 20 minutes.

9. A sulfur vulcanized rubber composition which is prepared by heating the composition of claim 1 to a temperature ranging from 100° C. to 200° C. in the presence of a sulfur vulcanizing agent.

10. The sulfur vulcanized rubber composition of claim 9 in the form of a tire, belt or hose.

* * * * *